US011551815B2

(12) United States Patent
Gagne et al.

(10) Patent No.: US 11,551,815 B2
(45) Date of Patent: Jan. 10, 2023

(54) RISK MONITORING SCORES

(71) Applicant: MEDICAL INFORMATICS CORPORATION, Houston, TX (US)

(72) Inventors: Vincent Gagne, Houston, TX (US); Alexander Csicsery-Ronay, Taos, NM (US)

(73) Assignee: Medical Informatics Corp., Houston, TX (US)

( * ) Notice: Subject to any disclaimer, the term of this patent is extended or adjusted under 35 U.S.C. 154(b) by 443 days.

(21) Appl. No.: 15/838,950

(22) Filed: Dec. 12, 2017

(65) Prior Publication Data

US 2019/0180875 A1 Jun. 13, 2019

(51) Int. Cl.
G16H 50/30 (2018.01)
G16H 10/60 (2018.01)
G16H 40/60 (2018.01)
G16H 10/20 (2018.01)

(52) U.S. Cl.
CPC .............. *G16H 50/30* (2018.01); *G16H 10/20* (2018.01); *G16H 10/60* (2018.01); *G16H 40/60* (2018.01)

(58) Field of Classification Search
CPC ......... G16H 50/30; G16H 10/60; G16H 40/60
USPC ............................................................ 705/2
See application file for complete search history.

(56) References Cited

U.S. PATENT DOCUMENTS

| 8,092,380 | B2* | 1/2012 | Rothman | G06F 19/322 600/300 |
| 8,100,829 | B2* | 1/2012 | Rothman | G06Q 50/22 600/300 |
| 8,170,888 | B2* | 5/2012 | Silverman | G06Q 50/22 705/3 |
| 8,355,925 | B2* | 1/2013 | Rothman | G06Q 50/22 705/2 |
| 8,403,847 | B2* | 3/2013 | Rothman | G06Q 50/22 600/300 |

(Continued)

OTHER PUBLICATIONS

Finlay G, Rothman M, Smith R. "Measuring the modified early warning score and the Rothman index: advantages of utilizing the electronic medical record in an early warning system" (2014). Journal of Hospital Medicine. (Year: 2014).*

(Continued)

*Primary Examiner* — Michael Tomaszewski
*Assistant Examiner* — Rachael Sojin Stone
(74) *Attorney, Agent, or Firm* — Schafer IP Law

(57) ABSTRACT

A user interface for clinical personnel provides selectable views of a plurality of medical risk scores. Questions whose answers are needed for calculation of those risk scores are asked in a question and answer area of the user interface, which allows some questions to be answered based on real time patient physiological data streams that are overridable by user provided answers. Where multiple risk score calculations require answers to the same question, the user provided answer may be supplied as an answer to the corresponding question for each risk score, rather than requiring the user to answer multiple times. Sparklines may be provided with the displayed risk scores to show trends in the risk score values, and may be updated in real time based on real time physiological data streams. The display of risk scores may visually distinguish between risk scores that have been validated and those are based on unvalidated answers to the questions.

17 Claims, 4 Drawing Sheets

(56) References Cited

U.S. PATENT DOCUMENTS

| | | | | |
|---|---|---|---|---|
| 8,454,506 | B2* | 6/2013 | Rothman | G06Q 50/22 600/300 |
| 9,892,444 | B2* | 2/2018 | Barday | G06Q 30/0609 |
| 10,483,003 | B1* | 11/2019 | McNair | G16H 50/30 |
| 2010/0131434 | A1* | 5/2010 | Magent | G06Q 10/06 706/11 |
| 2012/0008838 | A1* | 1/2012 | Guyon | G06T 7/62 382/128 |
| 2012/0041950 | A1* | 2/2012 | Koll | G06F 16/90332 707/728 |
| 2012/0296675 | A1* | 11/2012 | Silverman | G16H 50/50 705/3 |
| 2013/0179178 | A1* | 7/2013 | Vemireddy | G06Q 10/00 705/2 |
| 2013/0211858 | A1* | 8/2013 | Ohnemus | G16H 10/60 705/3 |
| 2013/0218045 | A1* | 8/2013 | Ironstone | A61B 5/4312 600/547 |
| 2014/0052474 | A1* | 2/2014 | Madan | G06F 19/3418 705/3 |
| 2014/0114680 | A1* | 4/2014 | Mills | G16H 50/30 705/2 |
| 2014/0214439 | A1* | 7/2014 | Young | G16H 50/30 705/2 |
| 2014/0316797 | A1* | 10/2014 | Biernacki | G16H 50/30 705/2 |
| 2015/0054628 | A1* | 2/2015 | Roth | G16H 40/67 340/10.4 |
| 2015/0142475 | A1 | 5/2015 | Rusin et al. | |
| 2015/0324900 | A1* | 11/2015 | Starikova | G06Q 40/02 705/35 |
| 2015/0324908 | A1* | 11/2015 | Starikova | G06Q 40/02 705/38 |
| 2016/0019360 | A1* | 1/2016 | Pahwa | G06F 19/3418 705/3 |
| 2016/0232321 | A1* | 8/2016 | Silverman | G16H 50/50 |
| 2016/0306965 | A1* | 10/2016 | Iyer | G06F 21/552 |
| 2018/0068083 | A1* | 3/2018 | Cohen | G16H 50/30 |
| 2019/0244684 | A1* | 8/2019 | Hussam | G16H 10/20 |
| 2020/0405148 | A1* | 12/2020 | Tran | A61B 3/0016 |

OTHER PUBLICATIONS

Int'l Search Report issued in copending PCT Application No. PCT/US2018/065021, dated Mar. 6, 2019, 18 pages.

Anonymous: "MDCalc—Medical calculators, equations, algorithms, and scores," Jun. 2, 2017, XP055559987, Retrieved from the Internet: URL:https://web.archive.org/web/20170602223302/https://www.mdcalc.com/.

& Anonymous: "HEART Score for Major Cardiac Events—MDCalc," Nov. 21, 2016, XP055559990, Retrieved from the Internet: URL:https://web.archive.org/web/20161121103158/http://www.mdcalc.com/heart-score-major-cardiac-events/.

& Anonymous: "TIMI Risk Score for UA/NSTEMI—MDCalc," Dec. 21, 2016, XP055560007, Retrieved from the Internet: URL:https://web.archive.org/web/20161221000005/http://www.mdcalc.com/timi-risk-score-ua-nstemi.

& Anonymous: "GWTG-Heart Failure Risk Score—MDCalc," Dec. 1, 2016, XP055560332, Retrieved from the Internet: URL:https://web.archive.org/web/20161201042249/http://www.mdcalc.com/gwtg-heart-failure-risk-score/.

Michael Rothman, "The Rothman Index Visualizing Patient Health," May 23, 2013, pp. 1-51, XP055559239, Retrieved from the Internet: URL:https://cdn2.hubspot.net/hubfs/1775295/Collateral%20/Publishing%20Documents%20/PRESENTATION_8_-_stanford_seminar_v3.pdf.

Michael Rothman, et al., "Sepsis as 2 problems: Identifying sepsis at admission and predicting onset in the hospital using an electronic medical record-based acuity score," Journal of Critical Care, vol. 38, Dec. 2, 2016, pp. 237-244.

* cited by examiner

RISK MONITORING SCORES

TECHNICAL FIELD

The present invention relates to the field of healthcare, and in particular to displaying a user-selectable plurality of medical risk scores.

BACKGROUND ART

In recent years, medical care units have become more data driven, using calculated evidence-based tools to help physicians and other clinical personnel. One of the better known commercial products is the Rothman Index, which captures data found in a hospital's electronic health record (EHR) and generates a graph that synthesizes routine vital signs, nursing assessments, and lab results, producing a single value, a risk score that can be used to track patient progress and detect subtle declines in health. Other risk scores have been devised for the medical community, such as a well-known collection of calculators freely available at mdcalc.com. These calculators are independently generated, with no synergism available when using multiple calculators. A better approach to presenting risk scores has been desired.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
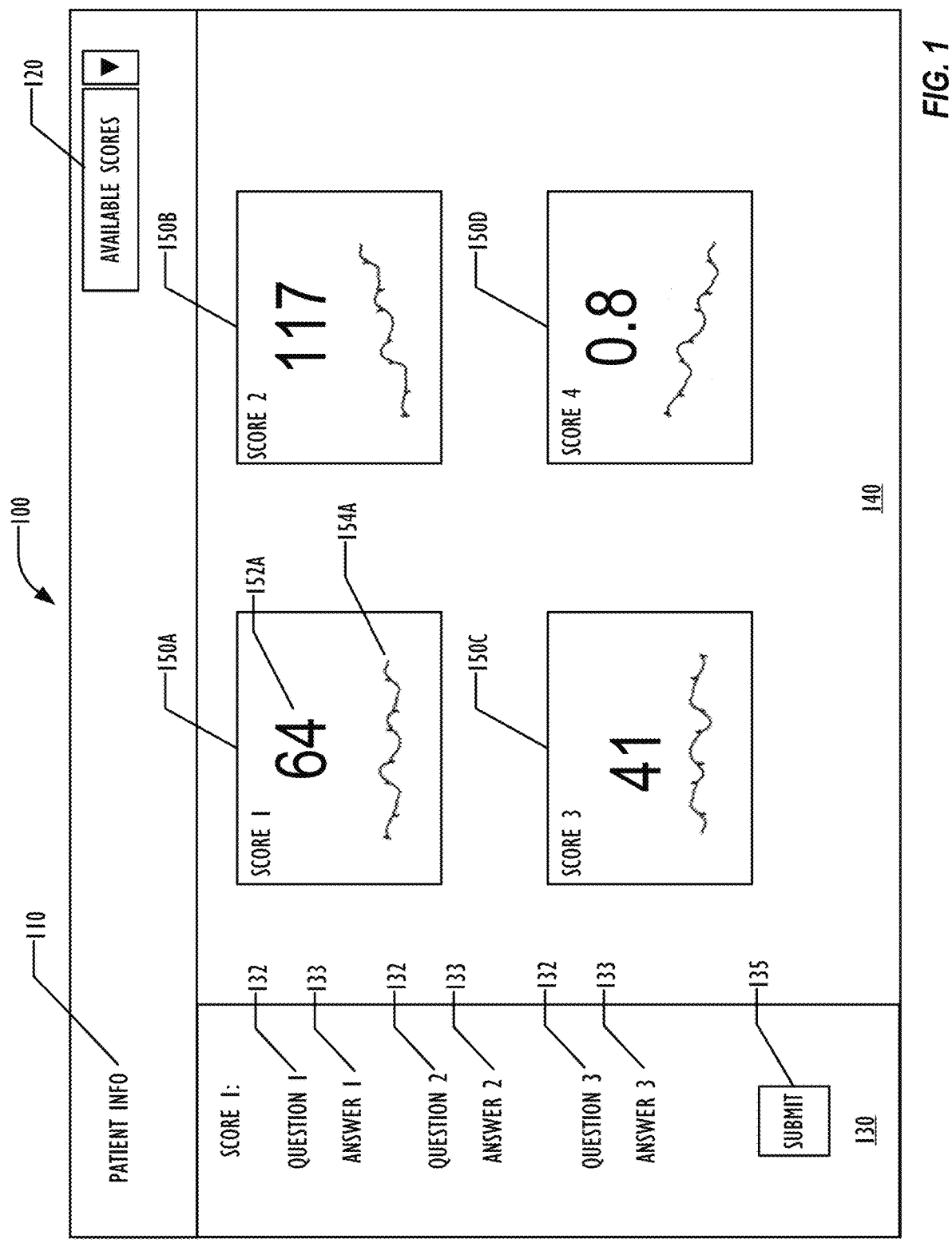
FIG. 1 is a block diagram illustrating a user interface for displaying a plurality of risk scores according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

The terms "a," "an," and "the" are not intended to refer to a singular entity unless explicitly so defined, but include the general class of which a specific example may be used for illustration. The use of the terms "a" or "an" may therefore mean any number that is at least one, including "one," "one or more," "at least one," and "one or more than one."

The term "or" means any of the alternatives and any combination of the alternatives, including all of the alternatives, unless the alternatives are explicitly indicated as mutually exclusive.

The phrase "at least one of" when combined with a list of items, means a single item from the list or any combination of items in the list. The phrase does not require all of the listed items unless explicitly so defined.

As used herein, the term "a computer system" can refer to a single computer or a plurality of computers working together to perform the function described as being performed on or by a computer system.

As used herein, the term "processing element" can refer to a single hardware processing element or a plurality of hardware processing elements that together may be programmed to perform the indicated actions. The hardware processing elements may be implemented as virtual hardware processing elements of a virtual programmable device hosted on a physical hardware device. Instructions that when executed program the processing element to perform an action may program any or all of the processing elements to perform the indicated action. Where the processing element is one or more multi-core processors, instructions that when executed program the processing element to perform an action may program any or all of the multiple cores to perform the indicated action.

As used herein, the term "medium" can refer to a single physical medium or a plurality of media that together store the information described as being stored on the medium.

As used herein, the term "memory" can refer to a single memory device or a plurality of memory devices that together store the information described as being stored on the medium. The memory may be any type of storage device, including random access memory, read-only memory, optical and electromechanical disk drives, etc.

A web-based user interface that relies upon an underlying vendor-agnostic platform provides a platform for a generalized risk score presentation interface. In one embodiment, the underlying vendor-agnostic platform is the SICKBAY™ platform from Medical Informatics Corp. (SICKBAY is a trademark of Medical Informatics Corp.) By allowing the platform to instantiate a web-based application that provides for a configurable monitoring station that can monitor risk scores from any number of patients from beds and facilities with equipment from any vendor, the deficiencies of central monitoring stations can be overcome. Because the risk score monitoring application is web-based, the risk score monitoring application can be used on nearly any type of device that can support web-based applications and display a graphical user interface, which includes fixed installations as well as mobile devices. Because the underlying platform can transform vendor-specific patient data into vendor-agnostic patient data, the configurable risk score monitoring application user interface can allow monitor watchers and care providers the ability to be more flexible in what they monitor.

FIG. 1 is a block diagram illustrating a graphical user interface (GUI) 100 for presenting a plurality of risk scores according to one embodiment. The GUI 100 allows presentation and display of a user-selectable collection of risk scores for a patient. In some embodiments, spark lines can be provided as a view showing trends in the risk scores. The GUI 100 patient data illustrated in FIG. 1 is illustrative and by way of example only, does not display actual patient information, and is not intended to display accurate medical conditions.

The arrangement and look of the GUI 100 is also illustrative and by way of example only. Any desired arrangement and presentation of the GUI elements may be used except as specifically set forth below and additional elements may be deployed in the GUI 100 as desired.

In this example, a patient information area 110 may be included, displaying any desired patient identifying information, such as, but not limited to, the patient's name, location in the clinical facility such as a bed number, a patient identifier, etc. The collection of risk scores available for display in the GUI 100 may be access in the element 120, illustrated in this example as a pull-down menu element. In such an embodiment, a user wishing to see a plurality of risk scores for the patient would select one or more items from the pull-down menu to add to the display. Other techniques for selecting the plurality of risk scores for display can be used, using techniques well-known in the GUI arts, for example check boxes.

As a risk score is added to the GUI 100, a question and answer area 130 may be displayed to allow the user to answer the questions that provide the values needed to compute the risk score. In the current example, three questions 132 are provided, along with three areas for answering those questions 133. The questions 132 asked vary with the risk score, and different risk score calculations may require any number of questions, depending upon the calculations performed to generate the risk score. The questions 132 generally relate to medical factors corresponding to the patient, such as age, physiological data values, etc., and may require subjective analysis by the user. For example, a HEART Score for Major Cardiac Events available on mdcalc.com includes the following questions:

History: slightly suspicious, moderately suspicious, or highly suspicious
EKG: normal, Non-specific repolarization disturbance, or significant ST depression
Age: <45, 45-64, or ≥65
Risk factors: no known risk factors, 1-2 risk factors, or ≥3 risk factors
Initial troponin: ≤normal limit, 1-2× normal limit, or >2× normal limit Although described herein as a question, each question 132 may be simply a data element related to the particular risk score, and may be presented in any desired way, using any desired type of GUI element for presenting the data element and allowing the user to provide an appropriate value for that data element, including typing a value, selecting a value from a list, etc.

In some embodiments, one or more of the questions associated with the risk score may be answered by providing real-time patient physiological data streams available from the underlying platform (described below in the discussion of FIG. 3), instead of the user typing or otherwise entering the value directly in an answer area. In some embodiments, the user may choose to accept the real time physiological sensor data values or may choose to enter an alternate value based on the user's consideration of the patient. If the user supplies a value, that value overrides the corresponding value supplied by the real-time patient physiological data stream.

Depending on the risk score calculation, more questions 132 may be needed for the calculation than there is room in the question and answer area 130. In such a situation, scrolling or other techniques may be used to navigate through the questions 132.

In one embodiment, after all of the questions 132 are answered, the user interacts with a user interaction element 135 (as illustrated in FIG. 1, a Submit button 135) to submit the answers 133 to the risk score calculator. This provides an indication that the user has validated the answers 133, including any of the answer 133 that may be provided by real time sensor data. The user interaction element 135 may be any desired type of user interaction element and labeled with any desired label indicating its purpose.

The plurality of selected risk score blocks 150 may be presented in the GUI 100 in a risk score area 140 separate from the question and answer area 130. In some embodiments, the question and answer area 130 may be visible only when the user has selected one of the risk scores, and be removed from the GUI 100 once the user has submitted the answer 133 using the question and answer area 130.

In FIG. 1, four risk score blocks 150A-150D are visible, but that number is illustrative and by way of example only, and any desired number of risk score blocks 150 may be displayed, subject to limits imposed by the GUI 100. Some embodiments may allow inclusion of more risk scores than may be simultaneously displayable on the display, and may provide means for navigating the risk score area 140, such as by the use of scroll bars (not shown in FIG. 1). Technique for allowing a user to navigate across an area that is larger than the display are well known in the art and need not be described in detail herein.

Each of the risk score blocks 150 typically includes an identifier for the risk score ("SCORE 1," "SCORE 2," "SCORE 3," and "SCORE 4" in FIG. 1, for example) and a numerical value for the risk score 152. In some embodiments, sparklines 154 may be included in the risk score blocks 150 to show the trend of that numerical value for the risk score 152.

As stated above, some risk scores may be calculated based at least in part on real time sensor data that produces real-time patient physiological data streams. Embodiments may automatically update the numerical value of the risk score 152 based on the updated real-time patient physiological data streams. This may occur without user interaction, so that the numerical value of the risk score 152 changes automatically, or may only change the presented numerical value of the risk score 152 when the user selects that risk score block 150.

Because data provided real-time patient physiological data streams may be changing automatically, without user review, embodiments may visually indicate that the numerical value of the risk score 152 is unvalidated information by use of color, shading, or some other type of GUI attribute, and that the numerical value of the risk score 152 is validated by similar use of color, shading, or some other type of GUI attribute if the user has submitted the risk score answer 133 by interacting with the submit button 135.

In some embodiments, the sparklines 154 may also include both validated and unvalidated data, including data based on real-time patient physiological data streams, and may include indications that at least some of the data in the sparklines 154 is unvalidated using color, shading, or some other type of GUI attribute. In some embodiments, portions of the sparkline 154 that correspond to validated risk score numerical values may be shown with one attribute and other portions of the sparkline 154 that correspond to unvalidated risk score numerical values may be shown with another attribute.

In some embodiments, the calculation of the risk scores 152 is performed in the browser that displays the GUI 100 in one of the personal devices 395 described in the discussion of FIG. 3 below. In other embodiments, the calculation of the risk scores 152 may be performed in a server, such as one of the servers 380-390 described below in the discussion of FIG. 3. In the server-calculated embodiments, risk scores 152 that are calculated at least in part from real time patient physiological data streams may be further compared against alarm thresholds and alarms generated in the underlying platform system.

Figure 2:
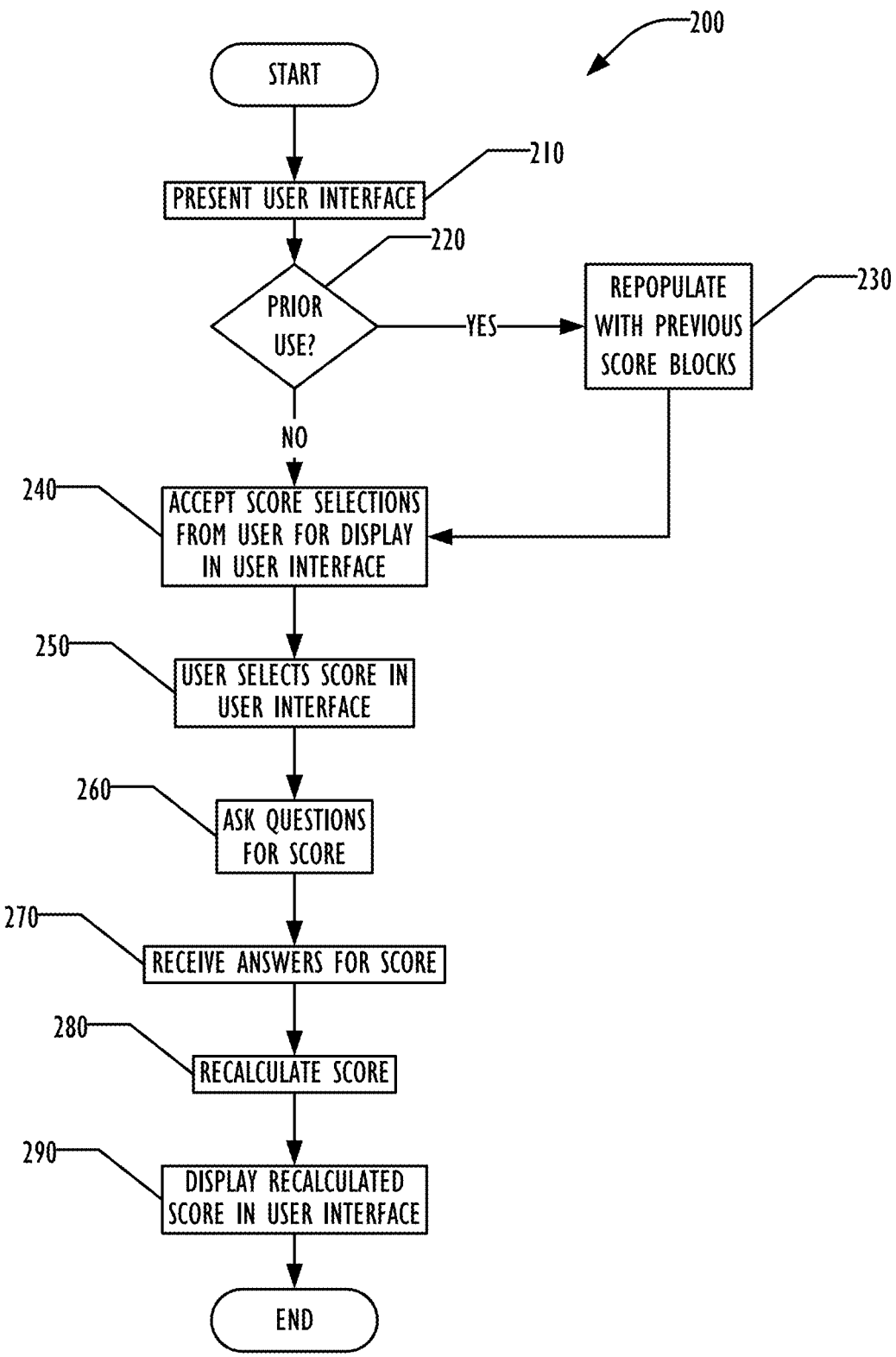
FIG. 2 is a flowchart illustrating a technique for displaying a plurality of risk scores according to one embodiment.

FIG. 2 is a flowchart 200 illustrating a technique for updating the GUI 100 according to one embodiment with a plurality of risk scores. In block 210 the GUI 100 may be presented for display. In some embodiments, the GUI 100 may be displayed on a display of the computer system generating the risk scores, but in other embodiments, the GUI 100 is a web-based GUI that can be displayed on any display using a browser, with a web server providing the GUI 100 for display in a browser of another device communicatively coupled to the web server, such as the personal devices 395 of FIG. 6 communicating with the servers 380-390, described below.

In block 220, a check is made whether the user has viewed the risk score display previously. If so, then in block 230 the GUI 100 may be repopulated with the risk score blocks 150 from the most recent use of the GUI 100, avoiding the need for the user to select each of the risk scores again. If the risk scores 152 displayed by those risk score blocks 150 are calculated at least in part on real time sensor data, unvalidated numerical scores and sparklines may be instantiated for those risk scores 152.

If the user has not previously used the GUI 100 then in block 240 the user may use the available score area 120 to select risk score blocks 150 to be shown in the risk scores area 140. If the risk scores area 140 is repopulated from previous usage, the user may make modifications in block 240 by rearranging, adding, or deleting the risk score blocks 150 for current desires.

In block 250, the user may select one of the displayed risk score blocks 150, allowing the user to enter the answers 133 to questions 132 in the question and answer area 130 for that risk score, with the questions asked in block 260 and the answers received in block 270. An advantage of collecting multiple risk scores in a single GUI 100 is that multiple risk scores may use the same questions. For example, two different risk scores may request a current heart rate or some other factor. In that situation, the user does not have to answer the corresponding question 132 multiple times, but the answers may be reused, reducing the need for user interaction with the GUI 100. Once the answers 133 have been received (including by copying from questions asked for other risk scores), the risk score may be recalculated in block 280 and displayed in the GUI 100 in block 290. In some embodiments, questions 132 that are duplicated in the calculation of multiple risk scores may be re-asked if the question 132 was previously answered more than a threshold amount of time in the past, rather than using the old answer 133 in the calculation of a different risk score.

Because different risk score calculators may use different language when asking essentially the same question, a mapping feature may be used to map similar questions 132 to each other, so that mere wording changes would not prevent the questions 132 from being recognized as the same question, and allowing reuse of the answers 133.

Figure 3:
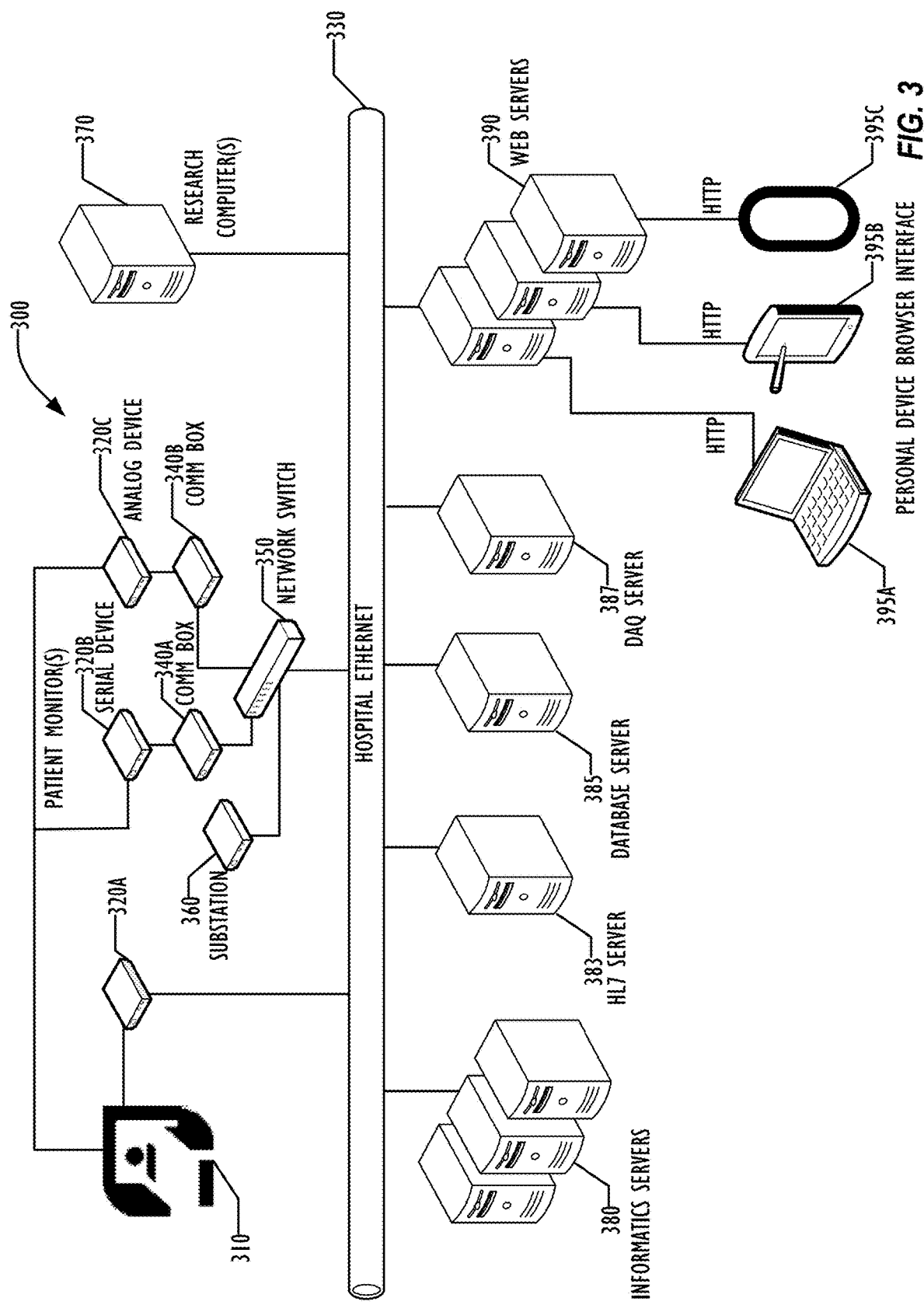
FIG. 3 is a block diagram of a system for collecting physiological data, generating the predictive information, and displaying the predictive information in a user interface as illustrated in FIGS. 1-4, according to one embodiment.

FIG. 3 is a block diagram illustrating a system 300 for collecting, archiving, and processing arbitrary data in a healthcare environment that can deploy a GUI 100 as described above, according to one embodiment.

As illustrated, there are five types of servers: the data acquisition (DAQ) server 387, the informatics server(s) 380, the database server 385, the Health Level 7 (HL7) server 383, and the web server(s) 390. Any number of any of the types of servers may be deployed as desired. All of the servers 380-390 connect to each other and the bedside monitors via one or more hospital networks 330. Although illustrated as a single hospital Ethernet network 330, any number of interconnected networks may be used, using any desired networking protocols and techniques.

Also connected to the hospital network 330 are a number of bedside monitors for monitoring physiological data for a patient in bed 310. These bedside monitors may include network connected monitors 320A, which can deliver digital physiological data to the hospital network 330, serial devices 320B, which produce digital data but are not directly connected to a network, and analog devices 320C, which produce analog data and are not directly connected to a network. Communication boxes 340A and 340B allow connecting the serial devices 320B and analog devices 320C, respectively, to the hospital network 330, typically through a network switch 350. In addition, a sub-station 360 may be also connected to the network 330 via the network switch 350 for performing data manipulation and time synchronization as described below. Any number of bedside monitor devices 320 may be used as determined advisable by physicians and other clinical staff for the patient in bed 310.

Although as illustrated in FIG. 3 the bedside monitors and associated communication devices are connected directly or indirectly to the hospital network 330, remote bedside monitoring devices may be used as part of the system 300, such as home monitoring devices, connected to the hospital network 330 indirectly through the Internet or through other communication techniques.

Additionally, one or more research computers 370 may be connected, directly or indirectly, to the hospital network 330, allowing researchers to access aggregated data collected from bedside monitors 320 for performing analytics and development.

The web servers 390 are configured for communicating with personal devices such as laptop 395A, tablet 395B, or smart phone 395C via a web browser interface using HyperText Transport Protocol (HTTP). The designation "personal devices" is not intended to be limiting, and the personal devices 395 may be any device capable of using a browser interface for displaying data. In one embodiment, the system 300 is a Sickbay Platform provided by Medical Informatics Corp. of Houston, Tex. More detail about the system 300 can be found in U.S. Pat. Pub. No. 2015/0142475A1, "Distributed Grid-Computing Platform for Collecting, Archiving, and Processing Arbitrary Data in a Healthcare Environment," U.S. patent application Ser. No. 14/548,433, filed Nov. 20, 2014, which is incorporated herein by reference in its entirety for all purposes.

Figure 4:
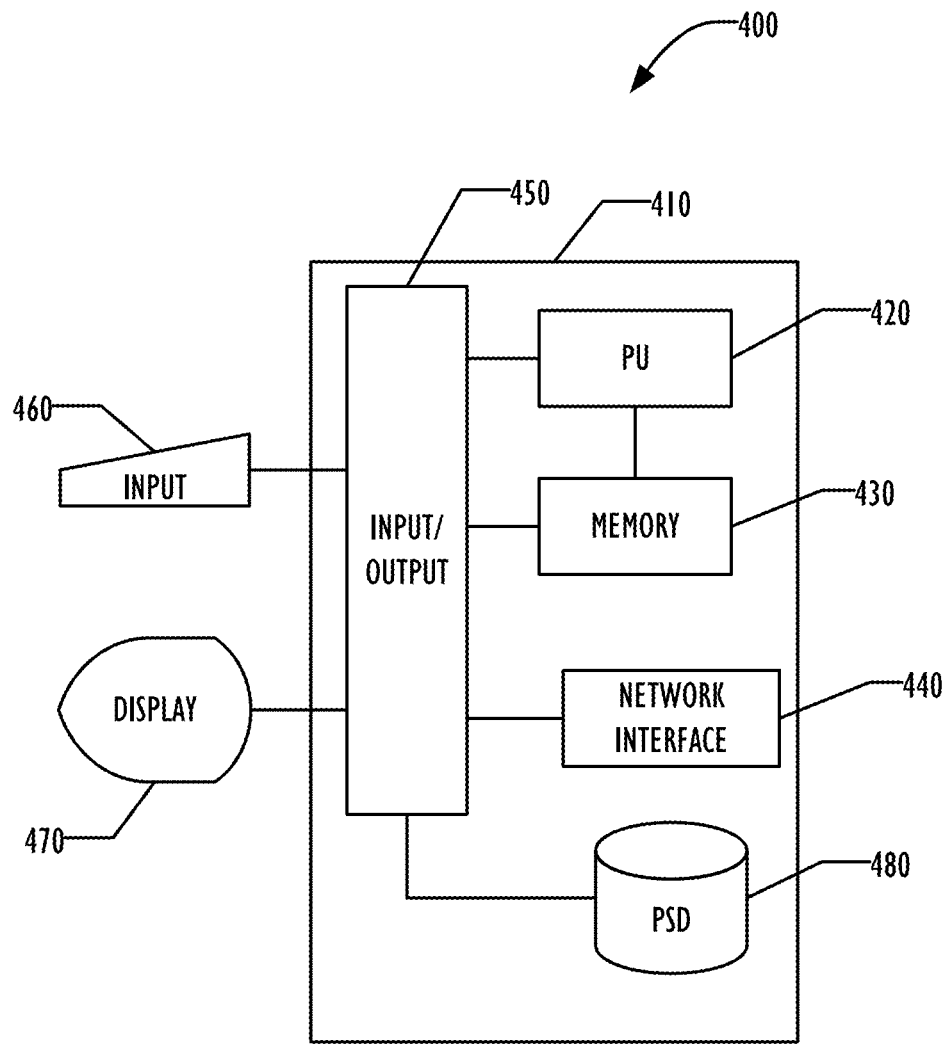
FIG. 4 is a block diagram of a programmable device used in the system of FIG. 3 according to one embodiment.

Referring now to FIG. 4, an example computer 400 for use as one of the servers 380-390 or personal devices 395 is illustrated in block diagram form. Example computer 400 comprises a system unit 410 which may be optionally connected to an input device or system 460 (e.g., keyboard, mouse, touch screen, etc.) and display 470. A program storage device (PSD) 480 (sometimes referred to as a hard disc) is included with the system unit 410. Also included with system unit 410 is a network interface 440 for communication via a network with other computing and corporate infrastructure devices (not shown). Network interface 440 may be included within system unit 410 or be external to system unit 410. In either case, system unit 410 will be communicatively coupled to network interface 440. Program storage device 480 represents any form of non-volatile storage including, but not limited to, all forms of optical and magnetic, including solid-state, storage elements, including removable media, and may be included within system unit 410 or be external to system unit 410. Program storage device 480 may be used for storage of software to control system unit 410, data for use by the computer 400, or both.

System unit 410 may be programmed to perform methods in accordance with this disclosure. System unit 410 comprises a processor unit (PU) 420, input-output (I/O) interface 450 and memory 430. Processor unit 420 may include any programmable controller device, such as microprocessors available from Intel Corp. and other manufacturers. Memory 430 may include one or more memory modules and comprise random access memory (RAM), read only memory (ROM), programmable read only memory (PROM), programmable read-write memory, and solid-state memory. One of ordinary skill in the art will also recognize that PU 420 may also include some internal memory including, for example, cache memory.

Embodiments may be implemented in one or a combination of hardware, firmware, and software. Embodiments may also be implemented as instructions stored on a computer-readable storage medium, which may be read and executed by at least one processing element to perform the operations described herein. A computer-readable storage medium may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

Embodiments may be implemented in one or a combination of hardware, firmware, and software. Embodiments may also be implemented as instructions stored on a computer-readable storage medium, which may be read and executed by at least one processing element to perform the operations described herein. A computer-readable storage medium may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

Embodiments, as described herein, may include, or may operate on, logic or a number of components, modules, or mechanisms. Modules may be hardware, software, or firmware communicatively coupled to one or more processing elements in order to carry out the operations described herein. Modules may be hardware modules, and as such, modules may be considered tangible entities capable of performing specified operations and may be configured or arranged in a certain manner. Circuits may be arranged (e.g., internally or with respect to external entities such as other circuits) in a specified manner as a module. The whole or part of one or more programmable devices (e.g., a standalone client or server computer system) or one or more hardware processing elements may be configured by firmware or software (e.g., instructions, an application portion, or an application) as a module that operates to perform specified operations. The software may reside on a computer readable medium. The software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Where modules are temporarily configured, each of the modules need not be instantiated at any one moment in time. For example, where the modules comprise a general-purpose hardware processing element configured using software; the general-purpose hardware processing element may be configured as respective different modules at different times. Software may accordingly program a hardware processor, for example, to constitute a particular module at one instance of time and to constitute a different module at a different instance of time. Modules may also be software or firmware modules, which operate to perform the methodologies described herein.

While certain exemplary embodiments have been described in details and shown in the accompanying drawings, it is to be understood that such embodiments are merely illustrative of and not devised without departing from the basic scope thereof, which is determined by the claims that follow.

We claim:

1. A method of integrating a plurality of medical risk scores for a patient, comprising:
   receiving one or more real-time patient physiological data streams from bedside monitoring devices associated with the patient;
   pre-populating a risk score area of a graphical user interface automatically, prior to presenting the graphical user interface, to a user with a plurality of medical risk scores from a collection of available medical risk scores that were presented in a most recent use of the graphical user interface by the user;
   updating at least some of the pre-populated plurality of medical risk scores automatically based on one or more of the one or more real-time patient physiological data streams
   modifying the risk score area responsive to a user input;
   receiving from one or more of the one or more real-time patient physiological data streams an answer to a first question of a plurality of questions associated with a first risk score of the plurality of medical risk scores;
   populating the answer to the first question in a first answer area of the graphical user interface automatically, prior to presenting the graphical user interface to the user;
   calculating the first risk score prior to presenting the graphical user interface to the user;
   presenting the calculated first risk score and the answer to the first question in the graphical user interface to the user;
   receiving in the graphical user interface user input with an alternate answer to the first question;

overriding the answer to the first question with the alternate answer;
recalculating the first risk score using the alternate answer;
validating the first risk score responsive to a validation user input; and
displaying validated risk scores in the graphical user interface visually differently from unvalidated risk scores.

2. The method of claim 1,
wherein receiving answers to the plurality of questions further comprises:
receiving a second one or more real-time patient physiological data streams received from a second one or more bedside monitoring devices associated with the patient;
receiving in a second answer area of the graphical user interface an answer to a second question of the plurality of questions provided by one or more of the second one or more real-time patient physiological data streams;
receiving in the graphical user interface user input with a second alternate answer to the second question; and
overriding the answer to the second question with the second alternate answer,
wherein calculating the first risk score comprises calculating the first risk score using the answer to the first question and the answer to the second question.

3. The method of claim 1, further comprising:
displaying a sparkline of values for the first risk score with the first risk score in the graphical user interface.

4. The method of claim 3, further comprising:
updating the sparkline by updating the first risk score based on data from the one or more real-time patient physiological data streams; and
displaying the sparkline as an unvalidated sparkline in the graphical user interface.

5. The method of claim 1, wherein the validation user input comprises selection of a graphical user interface element for submitting the alternate answer.

6. The method of claim 1, where the plurality of questions associated with the first risk score comprise a plurality of questions each associated with a component factor of a formula for calculating the first risk score.

7. A non-transitory machine readable medium, on which are stored instructions for displaying a plurality of medical risk scores for a patient, comprising instructions that when executed by a processing element cause a programmable device to:
receive one or more real-time patient physiological data streams from bedside monitoring devices associated with the patient;
pre-populate a risk score area of a graphical user interface automatically, prior to presenting the graphical user interface, to a user with a plurality of medical risk scores from a collection of available medical risk scores that were presented in a most recent use of the graphical user interface by the user;
update at least some of the pre-populated plurality of medical risk scores automatically based on one or more of the one or more real-time patient physiological data streams;
modify the risk score area responsive to receiving a user input;
receive from one or more of the one or more real-time patient physiological data streams an answer to a first question of a plurality of questions associated with a first risk score of the plurality of medical risk scores;
populate the answer to the first question in a first answer area of the graphical user interface automatically, prior to presenting the graphical user interface to the user;
calculate the first risk score prior to presenting the graphical user interface to the user;
present the calculated first risk score and the answer to the first question in the graphical user interface to the user;
receive in the graphical user interface user input with an alternate answer to the first question;
override the answer to the first question with the alternate answer;
recalculate the first risk score using the alternate answer;
validate the first risk score responsive to a validation user input; and
display validated risk scores in the graphical user interface visually differently from unvalidated risk scores.

8. The medium of claim 7,
wherein the instructions that when executed by the processing element cause the programmable device to receive answers to the plurality of questions further comprise instructions that when executed by the processing element cause the programmable device to:
receive a second one or more real-time patient physiological data streams received from a second one or more bedside monitoring devices associated with the patient;
receive in a second answer area of the graphical user interface an answer to a second question of the plurality of questions provided by one or more of the second one or more real-time patient physiological data streams;
receive in the graphical user interface user input with a second alternate answer to the second question; and
override the answer to the second question with the second alternate answer,
wherein the instructions that when executed by the processing element cause the programmable device to calculate the first risk score comprise instructions that when executed by the processing element cause the programmable device to calculate the first risk score using the answers to the answer to the first question and the answer to the second question.

9. The medium of claim 7, wherein the instructions further comprise instructions that when executed by the processing element cause the programmable device to:
display a sparkline of values for the first risk score with the first risk score in the graphical user interface.

10. The medium of claim 9, wherein the instructions further comprise instructions that when executed by the processing element cause the programmable device to:
update the sparkline by updating the first risk score based on data from the one or more real-time patient physiological data streams; and
display the sparkline as an unvalidated sparkline in the graphical user interface.

11. The medium of claim 7, wherein the validation user input comprises selection of a graphical user interface element for submitting the alternate answer.

12. The medium of claim 7, wherein the plurality of questions associated with the first risk score comprise a plurality of questions each associated with a component factor of a formula for calculating the first risk score.

13. A programmable device for displaying a plurality of medical risk scores for a patient, comprising:
- a processing element;
- a display, communicatively coupled to the processing element; and
- a memory, coupled to the processing element, storing instructions for displaying the plurality of medical risk scores for the patient, comprising instructions that when executed by the processing element cause the programmable device to:
  - receive one or more real-time patient physiological data streams from bedside monitoring devices associated with the patient;
  - pre-populate a risk score area of a graphical user interface automatically, prior to presenting the graphical user interface to a user with a plurality of medical risk scores from a collection of available medical risk scores based on that were presented in a most recent use of the graphical user interface by the user;
  - update at least some of the pre-populated plurality of medical risk scores automatically based on one or more of the one or more real-time patient physiological data streams;
  - modify the risk score area responsive to receiving a user input;
  - receive from one or more of the one or more real-time patient physiological data streams an answer to a first question of a plurality of questions associated with a first risk score of the plurality of medical risk scores;
  - receive in the graphical user interface user input with an alternate answer to the first question; and
  - override the answer to the first question with the alternate answer;
  - recalculate the first risk score using the alternate answer;
  - validate the first risk score responsive to a validation user input; and
  - display validated risk scores in the graphical user interface visually differently from unvalidated risk scores,
  - wherein the plurality of questions associated with the first risk score comprise a plurality of questions each associated with a component factor of a formula for calculating the first risk score.

14. The programmable device of claim 13,
wherein the instructions that when executed by the processing element cause the programmable device to receive answers to the plurality of questions further comprise instructions that when executed by the processing element cause the programmable device to:
- receive a second one or more real-time patient physiological data streams received from a second one or more bedside monitoring devices associated with the patient;
- receive in a second answer area of the graphical user interface an answer to a second question of the plurality of questions provided by one or more of the second one or more real-time patient physiological data streams;
- receive in the graphical user interface user input with a second alternate answer to the second question; and
- override the answer to the second question with the second alternate answer, wherein the instructions that when executed by the processing element cause the programmable device to calculate the first risk score comprise instructions that when executed by the processing element cause the programmable device to calculate the first risk score using the answers to the answer to the first question and the answer to the second question.

15. The programmable device of claim 13, wherein the instructions further comprise instructions that when executed by the processing element cause the programmable device to:
- display a sparkline of values for the first risk score with the first risk score in the graphical user interface.

16. The programmable device of claim 15, wherein the instructions further comprise instructions that when executed by the processing element cause the programmable device to:
- update the sparkline by updating the first risk score based on data from the one or more real-time patient physiological data streams; and
- display the sparkline as an unvalidated sparkline in the graphical user interface.

17. The programmable device of claim 13, wherein the validation user input comprises selection of a graphical user interface element for submitting the alternate answer.

* * * * *